United States Patent
Harandi (10) Patent No.: US 12,152,207 B2
(45) Date of Patent: Nov. 26, 2024

(54) FLUID BED STEAM CRACKING USING DIRECT HEATING

(71) Applicant: ExxonMobil Chemical Patents Inc., Baytown, TX (US)

(72) Inventor: Mohsen N. Harandi, New Hope, PA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 931 days.

(21) Appl. No.: 16/969,289

(22) PCT Filed: Jan. 18, 2019

(86) PCT No.: PCT/US2019/014257
§ 371 (c)(1),
(2) Date: Aug. 12, 2020

(87) PCT Pub. No.: WO2019/164609
PCT Pub. Date: Aug. 29, 2019

(65) Prior Publication Data
US 2021/0009903 A1 Jan. 14, 2021

Related U.S. Application Data

(60) Provisional application No. 62/633,242, filed on Feb. 21, 2018.

(30) Foreign Application Priority Data

Apr. 19, 2018 (EP) ..................................... 18168132

(51) Int. Cl.
*C10G 9/32* (2006.01)
*B01J 8/18* (2006.01)
*B01J 8/24* (2006.01)
*C07C 2/00* (2006.01)
*C07C 45/50* (2006.01)
(Continued)

(52) U.S. Cl.
CPC .............. *C10G 9/32* (2013.01); *B01J 8/1809* (2013.01); *B01J 8/24* (2013.01); *C07C 2/00* (2013.01); *C07C 45/50* (2013.01); *C10G 57/02* (2013.01); *B01J 2208/00106* (2013.01);
(Continued)

(58) Field of Classification Search
None
See application file for complete search history.

(56) References Cited

U.S. PATENT DOCUMENTS 3,848,016 A 11/1974 Niwa et al.
4,097,544 A * 6/1978 Hengstebeck ........ F28F 9/0229
422/208

(Continued)

OTHER PUBLICATIONS

"BASF Cracker Makes Ethylene from Crude Oil" *Industrial and Engineering Chemistry* (1961) vol. 53, No. 11, pp. 26A-28A.

*Primary Examiner* — In Suk C Bullock
*Assistant Examiner* — Alyssa L Cepluch (57) ABSTRACT

Systems and methods are provided for performing steam cracking on a feed while using direct heating of the reaction environment. The heating of the reaction environment can be achieved in part by transporting heat transfer particles from a heating zone to cracking zone. This can be performed in a fluidized bed reactor, a moving bed reactor, a riser reactor, or another type of reactor that can allow for catalyst movement and regeneration during operation.

18 Claims, 1 Drawing Sheet

(51) Int. Cl.
*C10G 57/02* (2006.01)
*C07C 11/00* (2006.01)

(52) U.S. Cl.
CPC ..... *B01J 2208/00327* (2013.01); *C07C 11/00* (2013.01); *C10G 2300/4006* (2013.01)

(56) References Cited

U.S. PATENT DOCUMENTS

| | | |
|---|---|---|
| 5,538,625 A | 7/1996 | Sigaud et al. |
| 5,952,539 A | 9/1999 | Seimandi et al. |
| 2005/0148806 A1* | 7/2005 | Cruijsberg ............... C10G 9/36 585/652 |
| 2006/0199987 A1* | 9/2006 | Kuechler ............... C10G 50/00 585/502 |
| 2011/0073524 A1* | 3/2011 | Cybulskis .............. C10G 55/04 208/113 |
| 2013/0338418 A1 | 12/2013 | Xu et al. |

* cited by examiner

FLUID BED STEAM CRACKING USING DIRECT HEATING

CROSS-REFERENCE TO RELATED APPLICATIONS

This application is a U.S. national phase application of PCT application No. PCT/US2019/014257 having a filing date of Jan. 18, 2019, which claims priority to and the benefit of U.S. provisional application Ser. No. 62/633,242 having a filing date of Feb. 21, 2018, the contents of both of which are incorporated by reference in their entirety.

FIELD

This invention relates to steam cracking of feeds using direct heating.

BACKGROUND

Steam cracking is a process for converting various feeds to light (e.g., $C_{3-}$, or $C_{4-}$) olefins. A typical steam cracker comprises a furnace that includes one or more reactor tubes that contain the feed. At least the final heating of the feed to the desired temperature for cracking is based on indirect heating. This heating is accomplished by combusting fuel using burners located in the furnace's firebox. This results in transfer of heat to the reactor tube walls, which then heats the feed in the tubes to produce a cracked gas containing light olefins. Since coke accumulates rapidly on the inner surfaces of the tubes, multiple furnaces are typically used in parallel so that at least one furnace can be off-line to allow for regeneration/cleaning (e.g., decoking) while other furnaces perform steam cracking. Conventionally, performing steam cracking on feeds containing a resid boiling range component can lead to still further shortened process cycles for a steam cracker due to excessive formation of coke on interior surfaces of the reactor tubes used in a conventional indirect heating steam cracker. As a result, feeds containing more than small amounts of resid boiling range components are conventionally considered to be unsuitable for use as feeds for steam cracking. Additionally, although steam cracking is effective for forming light olefins, it requires a substantial amount of site footprint, mainly resulting from furnace requirements such as the need for a thermally-efficient distribution of the firebox burners and reactor tubes, for generating flue gas at low pressure, and for preventing hot-spot formation on the reactor tubes. Using additional furnaces operating in parallel to maintain a substantially continuous production of cracked gas also contributes to the large footprint required for commercial scale steam cracking.

Direct heating can be used as an alternative to using indirect heating in furnaces is to perform steam cracking, such as by heating particles that are introduced directly into the steam cracking reaction environment. However, using direct heating for steam cracking can also present a variety of problems, e.g., an undesirable amount of coke formation. Other problems can be related to the nature of direct heating, where the fuel and/or its resulting flue gas used to provide heat may enter into the same reactor used for cracking. Mixing products from fuel combustion with the products of steam cracking dilutes the desired light olefins with flue gases such as CO, $CO_2$ and/or $N_2$. Still other difficulties can be related to a combination of controlling the temperature of the cracking conditions and controlling the residence time of the feed in the cracking conditions. Circulating hot solids to provide the heat requires high speed circulating systems at elevated temperature with significant potential for fouling and erosion. What is needed are systems and methods that can allow for improved control of the conditions during steam cracking with efficient heating without the drawbacks of the conventional systems. Optionally but preferably, such improved control can then potentially allow one or more problems related to the nature of direct heating to be mitigated or minimized A 1961 article from Industrial and Engineering Chemistry (Vol. 53, No. 11, pages 26-28) describes a method for steam cracking. The article describes direct heating using a fluidized bed of coke particles having a size distribution where 80% of the particles are between 0.1 mm and 0.5 mm, with particles of smaller than 0.1 mm being removed from the bed. The fluidized bed conditions are described as being sufficiently well-mixed to allow the bed to have a uniform temperature throughout the fluidized bed. The "cracking time" or residence time of the feed under the cracking conditions is described as being roughly 1 second, with a cracking temperature of 720° C. to 750° C. After cracking, the cracked gases enter a cyclone for separation of particles, followed by cooling to about 300° C. using a quench liquid corresponding to a column sump oil. Due in part to the desire to maintain a substantially uniform temperature in the particle bed, the cracking temperature is limited to a temperature of 720° C. to 750° C. Additionally, the particle size distribution is required to be relatively large due to assist with particle mixing in the bed. Still another difficulty can be the need to remove the coke particles from the cracking products prior to quenching the products. What is further needed is a direct heating method that can allow for higher cracking temperatures to generate a desired cracking product slate while still being able to control the amount of time feed is exposed to the cracking conditions to reduce or minimize overcracking.

U.S. Patent Application Publication No. 2013/0338418 describes direct catalytic cracking of crude oil by a temperature gradient process. A hydrocarbon feed is cracked in the presence of a cracking catalyst in a moving bed reactor. The moving bed reactor includes a vertical temperature gradient, so that the lowest temperatures are toward the lower portion of the reactor where the feed enters, and the highest temperatures are toward the top of the reactor. The cracking catalyst is generally described as a supported heterogeneous material (a solid substrate supporting active catalytic material) or a solid homogeneous material (entire material is catalytically active for cracking). Although no examples of a cracking catalyst are provided, the distinction between thermal cracking and fluid catalytic cracking is discussed. It is noted that the direct catalytic cracking method provided in U.S. Patent Application Publication No. 2013/0338418 involves both a) the use of a cracking catalyst, and b) a temperature profile where the temperature increases when moving up in the fluidized bed. What is further needed are systems and methods that can crack feedstock while reducing, minimizing, or eliminating the need for specialized cracking catalysts. What is additionally needed are systems and method that can avoid the need to have the highest temperatures at the top of the bed, so that improved control can be provided for exposure of the feed to cracking temperatures.

SUMMARY OF THE INVENTION

The invention concerns systems and processes for performing steam cracking using direct heating of the reaction environment, but while also allowing increased temperatures in the cracking zone and/or while also providing improved control over the time of exposure of the feed to cracking temperatures. This can allow for steam cracking of a variety of feeds while reducing or minimizing the difficulties encountered in conventional cracking processes.

The invention relates to the discovery that operating a steam cracker using direct heating with a cracking zone that is cooler than the heating zone can allow for an improved ability to perform steam cracking on heavy feeds, such as feeds containing a resid boiling range fraction (560° C.+). By using direct heating, cycle lengths can be improved as a substantial portion of the coke formed during steam cracking can be formed on the heat transfer particles that are used for a substantial portion of the direct heating. These heat transfer particles, such as silica particles, can then be passed into the heating zone. This allows the coke to be used as fuel for the steam cracker while also reducing or minimizing the amount of coke that builds up within the reaction system. It is noted that the heat transfer particles can correspond to convenient particles for heat transfer, as opposed to requiring particles with specific or specialized catalytic activity. This can reduce or minimize concerns about catalyst lifetime that would be present in a catalytic cracking system. Additionally, distribution of heat through the cracking zone can be improved by using smaller heat transfer particles while still providing a desired temperature profile.

Additionally or alternately, in some aspects the invention further relates to the discovery that by operating the heating zone to form at least some CO instead of $CO_2$, a beneficial amount of synthesis gas (CO and $H_2$) can be included in the cracked reaction products. In addition to reducing the total volume of flue gas generated relative to a conventional steam cracker, operating the heating zone to form synthesis gas can also facilitate integration of a direct heating steam cracking process with other refinery processes. For example, the presence of synthesis gas in the cracked product can allow a portion of the cracked product to be used as a feed for hydroformylation, without requiring addition of a separate synthesis gas feed. Optionally, the formation of synthesis gas can be facilitated by operating the steam cracker at an oxygen stoichiometric ratio of 1.2 or less, such as a ratio of 0.6 to 1.2.

Additionally or alternately, in some aspects the invention further relates to using heat transfer surfaces that are adjacent to and/or at least partially in contact with the particle bed from the cracking zone. This can allow for improved transfer of heat to the heat transfer surfaces in a quench zone, which can facilitate cooling the cracked reaction products rapidly to avoid excess cracking reactions. This can also allow the cracking zone and/or the heating zone to be operated at a higher temperature while still maintaining a desired level of control over the amount of exposure of the feed to cracking conditions. This can reduce or minimize the amount of overcracking of the feed, which would otherwise lead to production of less desirable cracking products. Having the quench zone adjacent to the cracking zone can be in contrast to conventional configurations, where separation of catalyst particles and/or coke is performed first, followed by a subsequent quenching that is performed after particle removal.

BRIEF DESCRIPTION OF THE DRAWING

The FIGURE shows an example of a reactor for performing steam cracking using direct heating.

DETAILED DESCRIPTION

Overview

Figure 1:
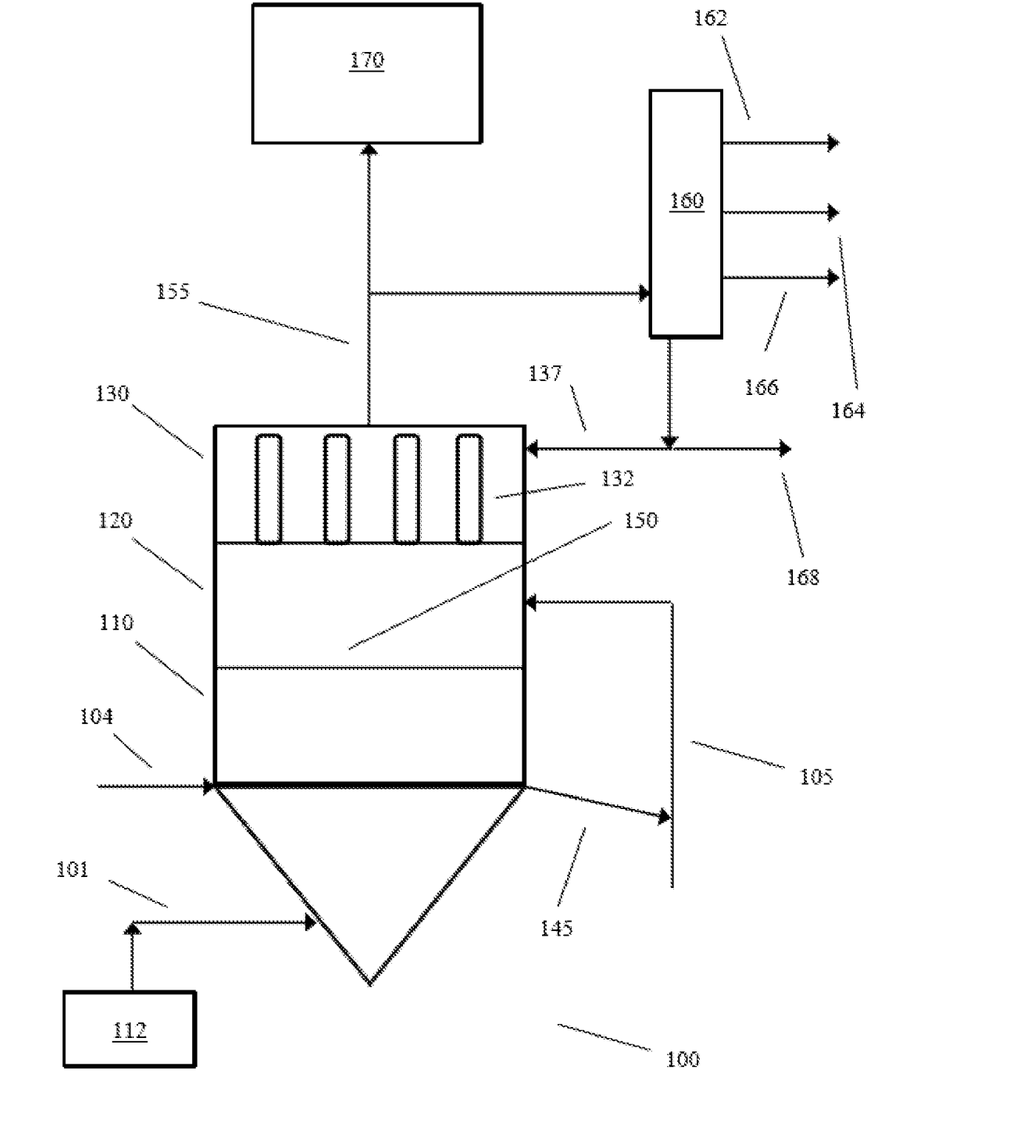

In various aspects, systems and methods are provided for performing steam cracking on a feed while using direct heating of the reaction environment, such as direct heating of the cracking zone of a reactor. The heating of the reaction environment can be achieved in part by transporting heat transfer particles from a heating zone to cracking zone. This can be performed in a fluidized bed reactor, a moving bed reactor, a riser reactor, or another type of reactor that can allow for catalyst movement and regeneration during operation. Examples of suitable heat transfer particles can include silica particles. A suitable fuel can be coke that forms on the silica particles during cracking. The coke on the silica particles can be at least partially removed (via combustion) in the heating zone. Optionally, an additional or supplemental fuel can also be introduced into the heating zone. Direct heating can provide a variety of advantages over indirect heating methods for steam cracking. For example, one of the difficulties in steam cracking with indirect heating is coke formation within the reactor tubes where cracking is performed. Steam crackers that operate with indirect heating typically do not have a mechanism to allow for removal of coke during operation. Thus, multiple steam cracker furnaces are often needed to allow for continuous operation, so that some furnaces can be taken offline periodically to allow for regeneration of the reaction tubes. By contrast, a steam cracker operated with direct heating can reduce or minimize down-time due to coke formation as a substantial portion of the coke will be deposited on the heat transfer particles. The particles can be circulated to the heating zone during operation, and the coke can be burned as fuel to maintain a desired temperature in the heating zone and/or cracking zone. This can reduce the refinery footprint that is needed for performing commercial scale steam cracking, as the multiple parallel furnaces typically used for steam cracking with indirect heating are not required.

During processing of a feed, the feed can be introduced into a cracking zone along with steam. Any convenient available fluid can be used to fluidize the catalyst bed, such as steam, a portion of the feed, and/or oxygen for burning of coke and/or additional fuel. The heating zone can be operated at a temperature greater than the cracking zone. After cracking, the reaction products can be passed into a quench zone to reduce or minimize further reaction of the cracked reaction products. In some aspects, the quench zone can include heat transfer surfaces, such as heat exchange tubes. Optionally, the heat transfer particles can be in contact with the heat transfer surfaces to facilitate faster cooling. For example, at least a portion of the heat transfer surfaces can be located within the fluidized bed and/or above and adjacent to the fluidized bed in a disengaging zone during operation. Having the heat transfer surfaces in contact with the fluidized bed and/or adjacent to the fluidized bed can improve the rate of cooling within the quench zone above the fluidized bed. Optionally, a quench liquid can also be used to further facilitate rapid cooling. The quench liquid is preferably injected above the quench zone tubes area and the quench can be a recycle stream, preferably a recycle stream corresponding to a heavy portion of the reaction effluent.

After cooling of the cracked products, various options are available for further separation and/or reaction of the cracked products. An initial separation can correspond to a gas-solids separation to remove entrained solids from the cracked product flow. In some aspects, the cracked products can be separated to form typical product streams from a steam cracking process, such as one or more light olefin streams containing $C_{4-}$ olefins. In some aspects, if CO is generated during burning of coke in the heating zone, a portion of the cracked products can be used as a synthesis gas type feed. In some aspects, at least a portion of the olefins can be oligomerized to form larger compounds.

It is noted that using direct heating for the cracking zone can result in introduction of the flue gas from the heating zone into the cracking zone. As a result, the separations of the cracked products can also include one or more separations to remove $CO_2$ and/or CO from the cracked products. Traditionally, the introduction of carbon oxides into the flue gas has been viewed as a negative feature of steam cracking reactors that operate with direct heating. However, reducing or minimizing the emission of carbon oxides is becoming increasingly important. If capture of carbon oxides is desired, using direct heating instead of indirect heating during steam cracking can actually be advantageous. For example, direct heating can reduce the amount of $CO_2$ produced, as direct heating is a higher efficiency method for achieving a given temperature in a reaction environment. Additional benefits with regard to reducing flue gas volume can be achieved by using an oxygen source with a lower nitrogen content than air. In some optional but preferred aspects, an oxygen stream with an $O_2$ content of 90 vol. % or more can be used instead of air.

Definitions

The term "catalyst" refers to a material, which under certain conditions of temperature or pressure increases the rate of specific chemical reactions. A catalyst may also be a material that performs as a physisorbent or chemisorbent for specific components of the feed stream.

The term "chemical reaction" refers to any process including the breaking or making of chemical bonds including a dissociation, recombination, or rearrangement of atoms.

The term "crude oil" refers to hydrocarbons formed primarily of carbon and hydrogen atoms. The hydrocarbons may also include other elements, such as, but not limited to, halogens, metallic elements, nitrogen, oxygen, or sulfur. Hydrocarbons derived from an oil-bearing formation may include, but are not limited to, kerogen, bitumen, pyrobitumen, asphaltenes, resins, oils, or combinations thereof.

The term "hydrocarbon" refers to an organic compound that includes primarily, if not exclusively, the elements hydrogen and carbon. Hydrocarbons may also include other elements, such as, but not limited to, halogens, metallic elements, nitrogen, oxygen, and/or sulfur. Hydrocarbons generally fall into two classes: aliphatic, or straight chain hydrocarbons, and cyclic, or closed ring hydrocarbons, including cyclic terpenes. Examples of hydrocarbon-containing materials include any form of natural gas, oil, coal, and bitumen.

The term "hydrocarbon stream" refers to a hydrocarbon or mixtures of hydrocarbons that are gases or liquids. For example, hydrocarbon fluids may include a hydrocarbon or mixtures of hydrocarbons that are gases or liquids at formation conditions, at processing conditions or at ambient conditions (15° C. and 1 atm pressure). Hydrocarbon fluids may include, for example, oil, natural gas, coalbed methane, shale oil, pyrolysis oil, pyrolysis gas, a pyrolysis product of coal, and other hydrocarbons that are in a gaseous or liquid state The term "zeolite" is defined to refer to a crystalline material having a porous framework structure built from tetrahedra atoms connected by bridging oxygen atoms. Examples of known zeolitic frameworks are given in the "Atlas of Zeolite Frameworks" published on behalf of the Structure Commission of the International Zeolite Association", $6^{th}$ revised edition, Ch. Baerlocher, L. B. McCusker, D. H. Olson, eds., Elsevier, New York (2007) and the corresponding web site, http://www/iza-structure.org/databases/. Under this definition, a zeolite can refer to aluminosilicates having a zeolitic framework type as well as crystalline structures containing oxides of heteroatoms different from silicon and aluminum. Such heteroatoms can include any heteroatom generally known to be suitable for inclusion in a zeolitic framework, such as gallium, boron, germanium, phosphorus, zinc, and/or other transition metals that can substitute for silicon and/or aluminum in a zeolitic framework.

Heat Transfer Particles and Reactor Inputs

In various aspects, steam cracking is performed by exposing a hydrocarbon feedstock to steam under temperature and pressure conditions that are suitable for cracking. The cracking zone in the reactor can include (but is not limited to) heat transfer particles, steam, hydrocarbon feedstock, flue gas from the heating zone, and optionally oxygen from the heating zone.

In some aspects, the reactor can correspond to a fluidized bed reactor that can allow for mixing of heat transfer particles between a heating zone and a cracking zone in the reactor. In such aspects, the flow conditions in at least the heating zone and the cracking zone can correspond to turbulent flow conditions to facilitate mixing between the zones. Such mixing can allow the heat transfer particles to carry heat from the heating zone into the cracking zone. Such mixing can also allow the heat transfer particles to return to the heating zone after deposition of coke on the particles, so that at least a portion of the deposited coke can be burned in the heating zone to generate additional heat. In other aspects, the steam cracking can be performed in a moving bed reactor or riser reactor. In such aspects, the heating zone and cracking zone can operate under substantially laminar flow conditions. In such aspects, the heat transfer particles can acquire coke as the particles pass through the cracking zone. After separation of the particles from the cracked products, the heat transfer particles can be returned to the heating zone where at least a portion of the deposited coke can be burned to generate heat.

The heat transfer particles can correspond to solids that are used to transport heat from a burning or heating zone of a reactor to the cracking zone. The heat transfer particles can optionally but preferably have little or no cracking activity. In some aspects, the heat transfer particles correspond to a refractory solid. In some aspects, the heat transfer particles include substantially no zeolitic framework structures, such as 0.1 wt. % or less of zeolitic framework structures. In some aspects, the heat transfer particles include substantially no supported metals with hydrogenation/dehydrogenation activity, such as 0.05 wt. % or less of such metals, or 0.01 wt. % or less. Examples of suitable materials for the heat transfer particles can include, but are not limited to, silica-containing particles (such as sand) and coke particles. In some aspects, the heat transfer particles can correspond to particles comprising silicon, such as in the form of silicon oxide. In some aspects, the heat transfer particles can have a size distribution so that 50 wt. % or more, or 60 wt. % or more, or 70 wt. % or more of the heat transfer particles have a characteristic length of 100 μm or less. It is noted that the characteristic length of a heat transfer particle can correspond to a maximum dimension across the particle. In the limit of a spherical particle, this would correspond to a particle diameter. This can correspond to a smaller particle size than some conventional heat transfer particle sizes, which can provide a greater exterior surface area for contacting other surfaces/liquids for performing heat transfer.

The hydrocarbon feedstock can be any convenient feedstock that includes $C_2$ or larger hydrocarbons. Thus, some suitable feedstocks can correspond to natural gas liquids, refinery liquefied propane gas, and/or other feedstocks containing a substantial portion (20 vol. % or more) of $C_2$-$C_5$ hydrocarbons. In some aspects, other suitable feedstocks can correspond to feedstocks containing high boiling components, such as coal, crude oil or other feedstocks containing a vacuum resid fraction. A resid fraction is defined herein as a fraction having a distillation point of 510° C. or more, or 535° C. or more, or 560° C. or more. In some aspects, a feedstock can include about 10 wt. % or more of a resid fraction (i.e., a T90 distillation point of 510° C. or more, or 535° C. or more, or 560° C. or more), or about 30 wt. % or more (i.e., a T70 distillation point of 510° C. or more, or 535° C. or more, or 560° C. or more), or about 50 wt. % or more (i.e., a T50 distillation point of 510° C. or more, or 535° C. or more, or 560° C. or more), or about 70 wt. % or more (i.e., a T30 distillation point of 510° C. or more, or 535° C. or more, or 560° C. or more). In some aspects, the feedstock can correspond to a resid fraction having a T10 distillation point of 510° C. or more, or 535° C. or more, or 560° C. or more. Distillation points described herein can be determined according to ASTM D2887 or, if D2887 is not suitable based on the nature of the sample, according to ASTM D7169. In some aspects, at least a portion of the feedstock can be used as the fluid for fluidization of the heat transfer particles. In some aspects, at least a portion of the feed can be introduced into the cracking zone of the reactor. In a preferred aspect, fluidization can be achieved using other fluids introduced into the reactor, and the feed can be introduced into the cracking zone of the reactor.

Steam can also be introduced into a reactor in order to provide suitable conditions for steam cracking. The amount of steam introduced can vary depending on the nature of the feed. Feeds with lower boiling ranges can be cracked with lower amounts of steam, while heavier feeds such as resid feeds can benefit from higher amounts of steam. Depending on the aspect, the amount of steam introduced into the reactor can be expressed as a ratio relative to the amount of feedstock for steam cracking. Suitable ratios of steam to hydrocarbon feed, on a weight basis, can range from 0.1 to 1.5, or 0.1 to 1.0, or 0.4 to 1.0, or 0.4 to 1.5, or 0.6 to 1.0. It is noted that a ratio 0.1 is somewhat low for the amount of steam in a conventional steam cracker. However, the additional flue gas from the heating zone serves as an additional diluent in the cracking zone, thus reducing the partial pressure of hydrocarbons in the cracking zone into desired and/or typical ranges that can favor olefin production. Thus, in some aspects, the steam to hydrocarbon ratio can be lower than expected based on the nature of the feed, such as a steam to hydrocarbon ratio of 0.1 to 0.6, or 0.1 to 0.4. In aspects where the feed corresponds to a resid feed, with a T10 distillation point of 510° C. or more and/or a T50 distillation point of 560° C. or more, the ratio of steam to hydrocarbon feed can be 0.6 to 1.5, or 0.8 to 1.5, or 1.0 to 1.5. The steam can be introduced into the reactor at any convenient location in the heating zone or cracking zone. Optionally, the steam can be used as at least a portion of the fluid for fluidizing the heat transfer particles. Preferably it is mixed with oxygen and/or feed before entering the reactor.

Oxygen can be introduced into the reactor in the heating zone to facilitate burning of coke and/or additional fuel in order to maintain a desired temperature in the various zones in a reactor. In some aspects, the amount of oxygen introduced into the heating zone can be greater than the stoichiometric amount that is used for burning of coke and/or additional fuel. This can result in some excess oxygen being present in the cracking zone. In some aspects, the amount of oxygen introduced into the heating zone can be limited so that partial combustion is performed on the coke and/or additional fuel in the heating zone. This can facilitate formation of additional CO, as opposed to $CO_2$, in the flue gas generated in the heating zone. It is noted that based on the presence of steam in the reaction environment, the water gas shift reaction can allow for production of $CO_2$ and $H_2$ in exchange for CO and $H_2O$. Thus, the relative amounts of CO and $CO_2$ in the flue gas may differ from the amounts generated during the combustion reactions in the heating zone.

In some aspects, oxygen can be introduced into the heating zone in the form of air. In other aspects, it can be desirable to reduce or minimize the amount of nitrogen introduced into the heating zone, as such nitrogen can eventually become part of the flue gas that enters the cracking zone. In such aspects, an air separation unit and/or another source of oxygen with reduced nitrogen content can be used as the oxygen source for the reactor. In some aspects, the oxygen content of the oxygen-containing stream introduced into the heating zone of the reactor can be 21 vol. % or more, or 25 vol. % or more, such as up to 30 vol. %. This can roughly correspond to the type of oxygen content present in air. In some aspects, an oxygen-containing stream with a higher oxygen content can be used, such as an oxygen content of 30 vol. % or more, or 35 vol. % or more, or 50 vol. % or more, such as up to 90 vol. % or preferably still higher. This can correspond to the type of oxygen content present in a stream from an air separation unit. In addition to characterizing the oxygen content, the nitrogen content of the oxygen-containing stream can also be characterized. In some aspects, the amount of nitrogen in the oxygen-containing stream can be lower than the amount present in air, so that the nitrogen content of the oxygen-containing stream can be 50 vol. % or less, or 30 vol. % or less, such as down to 10 vol. % or preferably still lower. Using an oxygen-containing stream with a reduced nitrogen content can provide substantial cost savings, as the excess nitrogen does not need to be heated, cooled, and/or compressed in any of the various locations in the reaction system where temperature or pressure changes occur. Additionally, reducing the amount of nitrogen reduces the complexity and cost of the recovery section and improves the ability to use an amine wash for $CO_2$ removal during separation of the cracked products.

One option for characterizing the amount of oxygen introduced into the heating or burning zone can be based on the ratio of the amount of oxygen introduced into the heating zone versus the amount of oxygen required for stoichiometric combustion of the coke and/or additional feed that is consumed in the heating zone. This is referred to herein as the stoichiometric oxygen ratio. Stoichiometric combustion is defined as sufficient oxygen to convert all carbon in the coke and/or additional feed into $CO_2$ plus convert all hydrogen in the coke and/or additional feed into $H_2O$. The amount of oxygen required for stoichiometric combustion can be determined using analytical techniques to determine the carbon and hydrogen content of any additional feed introduced into the heating zone. With regard to coke, the amount of carbon (and optionally hydrogen) in coke on particles can also be characterized. Additionally, the ratio of carbon to silicon in heat transfer particles sampled from locations prior to entering the heating zone and after exiting the heating zone can be used to determine the amount of coke being burned during operation. Alternatively, if the heat transfer particles correspond to coke, the amount of coke burned in the heating zone can be determined based on the average particle size of the coke prior to and after passing through the heating zone.

An amount of oxygen introduced into the heating zone that is sufficient for performing stoichiometric combustion with no excess oxygen remaining is defined herein as corresponding to a stoichiometric oxygen ratio of 1.0. If more oxygen is introduced than is needed for the combustion occurring in the heating zone, the stoichiometric oxygen ratio will be greater than 1.0. If less oxygen is introduced, the stoichiometric oxygen ratio will be less than 1.0. As an example, if the amount of oxygen introduced corresponds to the amount that is needed to convert hydrogen to $H_2O$ but only convert carbon to CO, the stoichiometric oxygen ratio can be between 0.6 and 0.8, depending on the hydrogen content of the feed.

In some aspects, the amount of oxygen introduced into the heating zone of the reactor can correspond to a stoichiometric oxygen ratio of 0.6 to 1.2, or 0.6 to 1.0, or 0.6 to 0.9, or 0.7 to 1.0, or 0.7 to 0.9, or 0.8 to 1.0.

Although not introduced into the reactor as a separate component, coke on the heat transfer particles can provide at least a portion of the fuel that is burned or combusted in the heating zone to generate heat. In addition to coke deposited on the heat transfer particles, in some aspects the heat transfer particles can correspond to coke particles.

In some aspects, additional fuel can be introduced into the heating zone of the reactor in order to maintain a desired temperature. Feeds that include larger amounts of lighter hydrocarbons can have a reduced or minimized tendency to form coke. For such feeds, burning of additional fuel may correspond to the majority of the heat generated in the heating zone. By contrast, little or no additional fuel may be needed for hydrocarbon feeds that include substantial amounts of resid. Any convenient additional fuel can be used. In some aspects, the additional fuel can correspond to a portion of the hydrocarbon feedstock.

The reactions in the heating zone can result in formation of a flue gas that passes from the heating zone to the cracking zone. This flue gas can correspond to an additional energy carrier for direct heating of the cracking zone. In aspects where substantially complete combustion is performed in the heating zone, the flue gas can substantially correspond to $H_2O$, $CO_2$, and any $N_2$ introduced into the heating zone along with the oxygen. In other aspects, a portion of the carbon oxides generated during burning of coke and/or additional fuel can correspond to CO. In such aspects, the flue gas can correspond to $H_2O$, $CO_2$, CO, $H_2$, and any $N_2$ introduced into the heating zone. Depending on the aspect, the amount of combined $H_2$ and CO in the cracked products prior to performing separations can correspond to 0 vol. % to 99 vol. % of the gas volume, or 1.0 vol. % to 99 vol. %, or 5.0 vol. % to 99 vol. %, or 1.0 vol. % to 50 vol. %, or 5.0 vol. % to 50 vol. %. Optionally, some $O_2$ may also be present in the flue gas that enters the cracking zone.

Due in part to the presence of additional flue gas in the cracked product, the amount of olefins in the cracked product can be relatively low. In various aspects, the $C_{4-}$ olefin content in the cracked product and/or the quenched cracked product can correspond to about 20 vol. % or less of the cracked product and/or the quenched cracked product, or about 16 vol. % or less, or about 12 vol. % or less, such as down to 1 vol. % or possibly still lower.

Heating Zone and Cracking Zone Conditions

In various aspects, the reactor for performing steam cracking using direct heating can include a heating zone and a cracking zone that are in fluid communication. The heating zone and cracking zone can be adjacent within the reactor, with the cracking zone located above the heating zone (but downstream relative to the net flow in the reactor). In some aspects, the fluidized bed in the heating zone can be in direct contact with the fluidized bed in the cracking zone, so that circulation overlap can occur between the zones. In some aspects, the fluidized bed in the heating zone can be segregated from the fluidized bed in the cracking zone, such as by including a gas distribution system between the heating zone and the cracking zone. In some aspects, some cracking can occur in the heating zone and/or some combustion can occur in the cracking zone. The heating zone, cracking zone, and quench zone will be described here with regard to a fluidized bed configuration for convenience in illustrating the nature of the zones. It is understood that a similar configuration can be achieved in a reactor that involves different fluidization regimes in the heating zone and/or cracking zone.

In a fluidized bed reactor, the boundary between the heating zone and the cracking zone may not be sharp, as there may be a region of overlap between the zones where both combustion of hydrocarbons and cracking of hydrocarbons is occurring. In some aspects where the fluidized beds for the heating zone and cracking zone are in direct contact, the boundary between the cracking zone and the heating zone can be defined, for example, as the mid-point of the fluidized bed within the reactor, based on the bottom of the fluidized bed and the top of the fluidized bed. It is noted that under this definition, some combustion may occur within the cracking zone and/or some cracking may occur within the heating zone. In some aspects where a distributor plate or other gas distribution system components are included, the boundary between the heating zone and the cracking zone can be defined based on the boundaries formed by the gas distribution system. With regard to the boundary between the cracking zone and the quench zone, the boundary is defined herein as the lower of a) the top of the fluidized bed and b) the bottom of any heat transfer surfaces that extend into the fluidized bed. It is noted that the cracking reaction benefits from a low residence time and heavier molecules require lower severity to crack. In one aspect of this invention, one or more lighter cracking feed streams can enter the lower part of the cracking zone to be exposed to the highest temperatures in the cracking zone for reaction. These lighter cracking feeds streams can then optionally provide additional dilution and turbulence for processing of one or more heavier feeds that enter at a higher position in the bed. In addition, the diameter of the cracking zone and combustion zone can be different to allow for the desired fluid-bed regime of operations as well as appropriate residence times.

The heating zone or combustion zone can be operated at an average temperature of about 1400° F. (~760° C.) to about 3500° F. (~1900° C.), or about 800° C. to about 1500° C., or about 850° C. to about 1100° C. The average temperature is defined as the average of the temperature at the bottom of the heating zone (i.e., the bottom of the fluidized bed) and the temperature at the top of the heating zone, which corresponds to the boundary between the heating zone and the cracking zone. The temperature can be increased by preheating or can be decreased by reducing preheating and/or removing heat from the fluid-bed in coils or by solid coolers. The temperature in the heating zone can be selected so that a desired temperature and circulation rate are maintained in the cracking zone. Coke from the heat transfer particles can serve as at least a portion of the fuel that is burned or combusted in the heating zone. In some aspects, additional fuel can be introduced into the heating zone. The burning or combustion reaction in the heating zone can generate a flue gas, as described above. The pressure in the heating zone can be any convenient pressure that is consistent with the target operating pressure in the cracking zone of the reactor.

The cracking zone can be operated at an average temperature of about 1100° F. (~590° C.) to about 1950° F. (~1060° C.), or about 650° C. to about 1060° C., or about 760° C. to about 1060° C., or about 800° C. to about 1060° C. The average temperature in the cracking zone is defined as the average of the temperature at the bottom of the cracking zone and the temperature at the top of the cracking zone, which corresponds to the bottom of the quench zone. In various aspects, the average temperature in the cracking zone can be lower than the average temperature in the heating zone by 10° C. to 300° C. More generally, in various aspects the average temperature in the cracking zone can be lower than the average temperature of the heating zone by 50° C. to 1500° C., or 100° C. to 500° C., or 200° C. to 400° C., or about 100° C. or more, or by about 300° C. or less.

The pressure in the cracking zone can be about 100 psig (~700 kPa-g) or less, or about 600 kPa-g or less, or about 300 kPa-g or less, or about 150 kPa-g or less, such as down to about 50 kPa-g or possibly still lower.

The residence time for feedstock in the cracking zone can vary depending on the nature of the feed. Suitable residence times can correspond to about 0.1 seconds to about 5.0 seconds, or about 0.3 seconds to about 2.0 seconds, or about 0.5 seconds to about 1.5 seconds, or about 0.7 seconds to about 1.0 seconds. Depending on the aspect, this type of residence time can correspond to a fluidized bed of a relatively short bed height.

The conditions in the cracking zone can be selected to generate a desired amount of cracking. For conventional steam cracker feeds, so that 10 wt. % or less of the feed corresponds to a resid fraction (a T90 distillation point of 560° C. or higher), the conditions in the cracking zone can be characterized based on the amount of conversion of paraffins in the feed to olefins. In such aspects, the cracking zone conditions can be selected for conversion of 40 wt. % or more of the paraffins in the feed to olefins, or 50 wt. % or more, or 60 wt. % or more, such as up to 80 wt. % or possibly still higher. In other aspects, the feed can correspond to a feed including 10 wt. % or more of a resid fraction (a T90 distillation point of 560° C. or less), such as 30 wt. % or more (T70 distillation point of 560° C. or less), or 50 wt. % or more (T50 distillation point of 560° C. or less). In such aspects, the cracking conditions can be characterized based on the amount of feed conversion that is performed relative to a conversion temperature of 560° C. In such aspects, the amount of conversion relative to 560° C. can be 20 wt. % or more, or 40 wt. % or more, such as up to 70 wt. % or possibly still higher. It is noted that the olefin yield is related to the reaction severity.

Conventional steam cracking furnaces cannot process resid containing feed streams since the tubes foul too quickly. By contrast, a direct heating processing configuration as described herein can not only allow resid to be processed, such a configuration can also attain a better selectivity at constant steam addition rate. This can be due in part to the dilution aspect of the flue gas mixing with the reactant and/or due in part to metals in resid laying on the solid particles and exhibiting some dehydrogenation activity. Therefore, the selectivity in a direct heating configuration as described herein can be at least as high as a conventional steam cracking configuration while also allowing for higher temperature operation, which can be beneficial for increasing or maximizing light olefins yield.

Quench Zone and Gas-Solid Separation

After forming cracked products, the cracked products can continue to travel up through the reactor into a quench zone. The quench zone can cool the cracked products preferably to below 500° C. in order to slow the coke forming reaction and/or to reduce or minimize further cracking. In some aspects, this cooling can be achieved in part by including heat transfer surfaces in the quench zone. In some aspects, the cooling can be achieved in part by adding a quench liquid to the quench zone.

Heat transfer surfaces in the quench zone can correspond to any convenient type of surfaces suitable for reducing the temperature of the cracked products after leaving the cracking zone. In some aspects, the heat transfer surfaces can correspond to heat exchange tubes. The fluid inside the heat exchange tubes can correspond to water, such as steam for use in fluidizing the bed; or the fluid inside the heat exchange tubes can correspond to feedstock prior to being passed into the reactor; or a combination thereof. Additionally or alternately, the heat transfer surfaces can correspond to fins or other heat transfer structures.

In some aspects, at least a portion of the heat transfer surfaces can be located within the fluidized bed or just above the fluidized bed (i.e., adjacent) in the reactor. This can increase the rate of heat transfer surfaces due to heat transfer with a condensed phase (solid particles colliding with the surface) as opposed to relying only on heat transfer between gas phase products and the surfaces.

In addition to or as an alternative to heat transfer surfaces, in some aspects a quench liquid can be introduced into the quench zone. A suitable quench liquid can be, for example, the feedstock and/or a heavier portion of the product that is recovered after separating solids from the cracked products. For example, when the feed includes a resid boiling range portion, the quench liquid can correspond to a 350° C.+ portion of the cracked product. It is noted that introduction of a quench liquid into the quench zone can occur before and/or after the cyclones. It is optional but preferable to start quenching before the cyclones to minimize residence time at temperatures that are high enough cause fouling. However, this can require more quench duty since the stream prior to entering cyclones can contain solid particles.

After reducing the temperature of the cracked products, the cracked products can be separated in one or more separation stages. An initial type of separation can correspond to a gas-solid separation. Cyclone separators are an example of a suitable structure for performing a gas-solid separation. The gas-solid separation can be used to separate heat transfer particles that are entrained in the cracked products from the rest of the product flow. Any condensed phase liquids present in the cracked products at the temperatures present in the cyclone separators can also be separated out. Such liquid products can be suitable for use, for example, as a quench liquid, or such liquid products can be returned to the cracking zone for further cracking.

Other separation stages can be used for separation of cracked products into various types of product streams. One conventional type of separation can be to separate flue gas components, such as $CO_2$, from the cracked products. $CO_2$ can be removed using an amine separator or another convenient type of $CO_2$ separator. Another type of separation can be to separate a light olefin stream ($C_2$-$C_4$ olefins) from the remaining cracked products. This can be performed, for example, using a cold box or other similar type of separator.

The FIG. shows an example of a fluidized bed reactor including a heating zone, a cracking zone, and a quench zone. In the FIG. a fluidizing stream 102 including oxygen-containing gas and steam is introduced into reactor 100 below the level of the bottom of the fluidized bed 150. Optionally, steam could be introduced in any other convenient location suitable for assisting with fluidizing the bed 150 of heat transfer particles and/or suitable for achieving a desired hydrocarbon concentration in the cracking zone. Optionally, supplemental fuel 104 can be introduced near the bottom of the fluidized bed 150. Optionally, the oxygen-containing gas can correspond to a stream from an air separation unit 112. The fluidized bed 150 includes a burning or heating zone 110, a cracking zone 120, and a quench zone 130.

Steam cracker feed 105 can be introduced into cracking zone 120. In the FIG., the steam cracker feed is shown as being introduced into roughly the middle of the cracking zone. Optionally, a portion of hydrocarbon feed (not shown) can also be introduced near the bottom of the cracking zone to better assist with fluidizing the bed of heat transfer particles. Optionally, such a portion can correspond to a lower boiling range portion of the hydrocarbon feed. Prior to entering cracking zone 120, the steam cracker feed 105 is mixed with a withdrawn stream 145 of heat transfer particles. The stream 145 of heat transfer particles is withdrawn from the burning zone 110 (or heating zone) of the fluidized bed 150. In the burning zone 110, at least a portion of the coke that is deposited on the heat transfer particle is burned to generate heat. The burned heat transfer particles can then be recycled to the cracking zone for further heat transfer.

After being exposed to the cracking zone, the cracked products can pass into the quench zone 130. Quench zone 130 includes a plurality of heat transfer surfaces 132. In the FIG., the heat transfer surfaces 132 stop at the top of fluidized bed 150. In some aspects, a portion of the fluidized bed 150 can be in the quench zone, based on at least a portion of the heat transfer surfaces being within the fluidized bed. The quenched cracked products can then be passed into one or more separation stages 160 for product recovery. The separation stages can generate a $CO_2$-containing stream 162, an olefin-containing stream 164, and one or more additional streams 166. In some aspects, the one or more additional streams 166 can include an unconverted product stream 168 that can be used, for example, as a quench stream 137. Optionally, a portion of the cracked products can be passed into an additional synthesis stage 170. The additional synthesis stage 170 can correspond to, for example, a hydroformylation stage or an oligomerization stage.

Formation of Additional Products—Oligomerization

In some optional aspects, the cracked products can undergo some further processing in addition to separations. For example, the cracked products can include various small olefins, such as ethylene, propylene, and/or other $C_{5-}$ olefins. At least a portion of the cracked product stream can be exposed to an oligomerization catalyst to form higher molecular weight compounds from the small olefins. Any convenient type of oligomerization catalyst and/or conditions can be used. Optionally, the oligomerization can selectively be performed on olefins of a desired size by performing separations prior to oligomerization. For example, a cooling chamber or another type of separator can be used to separate $C_{4+}$ olefins from $C_2$ and $C_3$ olefins in the cracked products. The fraction containing the $C_2$ and $C_3$ olefins can then be exposed to an oligomerization catalyst under conventional oligomerization conditions. Alternatively, it could be desirable to perform separations to generate a fraction containing $C_2$ olefins for oligomerization. In a preferred aspect, a light product fraction containing $C_{5-}$ or $C_{6-}$ light hydrocarbons (including olefins) without any separation of $CO_2$ can be contacted with the oligomerization catalyst. In such an aspect, the olefins in the light product fraction can be upgraded without expensive separation(s) of $CO_2$ from the light hydrocarbons. The remaining hydrocarbon gases after oligomerization can be substantially less expensive to separate from the $CO_2$, if desired, or the remaining light hydrocarbon gases can be used as a fuel gas.

Other types of additional products can become available if the heating zone is operated under oxygen-lean conditions so that CO is formed in the heating zone. If steam is present, a portion of the CO can react with steam to form $H_2$ and $CO_2$. The resulting flue gas can therefore include $H_2$ and CO. These gases can become part of the cracked products that are passed into the separation stages. One option for recovering the $H_2$ and CO from the other cracked products can be to oligomerize the olefins to form heavier compounds. The $H_2$ and CO can then be recovered in a remainder product separated from the oligomerized products by a conventional distillation.

The oligomerization can be performed by any convenient method. Due to the presence of the additional flue gas in the cracked product, the oligomerization conditions can optionally but preferably correspond to oligomerization conditions suitable for use with relatively dilute olefin streams. For example, in some aspects the oligomerization conditions can include conditions similar to those in the Mobil Olefins to Gasoline (MOG) process. The cracked product fraction from the direct heating steam cracking can have an olefin content of 15 vol. % or less. A variety of temperatures can be suitable for oligomerization in an MOG process, such as temperatures of about 215° C. to about 540° C. The pressure can be any convenient pressure from about 50 kPa-a to about 2000 kPa-a, so that the cracked product can be used as a feed to oligomerization at a pressure similar to the exit pressure from the steam cracker. For an MOG process, the oligomerization catalyst can correspond to a catalyst with a medium pore zeolitic framework structure, such as an MFI (ZSM-5) framework structure. The zeolitic framework structure catalyst can have an alpha value of about 2 to about 35, or about 5 to about 10. It is noted that an MOG process is an example of a suitable oligomerization process for integrated use in processing of an effluent (or a portion of an effluent) from a direct heating steam cracking process. In other aspects, any other convenient type of oligomerization conditions for performing olefin oligomerization on a feed containing a substantial portion of non-olefin components may be used.

Alpha value is a measure of the acid activity of a zeolite catalyst as compared with a standard silica-alumina catalyst. The alpha test is described in U.S. Pat. No. 3,354,078; in the Journal of Catalysis, Vol. 4, p. 527 (1965); Vol. 6, p. 278 (1966); and Vol. 61, p. 395 (1980), each incorporated herein by reference as to that description. The experimental conditions of the test used herein include a constant temperature of about 538° C. and a variable flow rate as described in detail in the Journal of Catalysis, Vol. 61, p. 395. Higher alpha values correspond with a more active cracking catalyst.

By using an oligomerization method that is suitable for use with a dilute olefin feed, the olefins from the cracked product can be converted to heavier liquid products (i.e., gasoline and/or diesel boiling range products) without requiring prior separation of $CO_2$ and/or other non-olefin compounds from the cracked product. Thus, the combination of direct heating steam cracking with olefin oligomerization can provide a method for upgrading a feed that is not suitable for processing in a conventional steam cracker.

Formation of Additional Products—Hydroformylation

Still another option can be to pass at least a portion of the cracked product stream to a hydroformylation stage to form aldehydes from olefins, $H_2$, and CO. In order to improve selectivity for using ethylene as the olefin for hydroformylation, one or more separations can be performed to separate at least a portion of the $C_{3+}$ or $C_{4+}$ olefins from the cracked products. The remaining olefins and CO can then be exposed to a hydroformylation catalyst under conventional hydroformylation conditions.

Steam cracker feeds have previously been proposed for use as a feed for hydroformylation, in combination with a separate synthesis gas stream. In some aspects, the cracked product streams generated by direct heating steam cracking as described herein can be advantageous over conventional steam cracker product streams due to the presence of synthesis gas in the flue gas from combustion. As a result, a separate synthesis gas stream is not needed to perform hydroformylation on a cracked product stream (or a portion thereof) formed by direct heating steam cracking as described herein.

U.S. Pat. No. 6,049,011 describes an example of conditions suitable for performing hydroformylation on a dilute ethylene feed. U.S. Pat. No. 6,049,011 is incorporated herein by reference for the limited purpose of describing hydroformylation conditions suitable for use with a dilute olefin feed, such as a steam cracking feed, in the presence of synthesis gas. Briefly, hydroformylation can be performed using a stream comprising $C_2$ olefins, $H_2$, and CO that is formed by separating the stream from a cracked product. The stream can be exposed to a hydroformylation catalyst, such as low valence rhodium complexed with CO and triorganophosphorus ligand(s), at relatively mild temperature and pressure conditions, such as about 50° C. to 200° C. with a pressure of 0.05 MPa-a to 50 MPa-a.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:
1. A method for performing steam cracking using direct heat transfer, comprising:
  fluidizing a bed of heat transfer particles with a fluidizing gas comprising one or more of steam, oxygen, and a first portion of a hydrocarbon feedstock, the fluidized bed of heat transfer particles comprising a heating zone and a cracking zone above the heating zone;
  exposing the fluidized bed of heat transfer particles to oxygen in the heating zone under oxidizing conditions to generate a temperature in the heating zone of about 760° C. to about 1900° C., at least a portion of the heat transfer particles in the heating zone comprising coke;
  exposing at least a portion of the hydrocarbon feedstock to the fluidized bed of heat transfer particles in the presence of steam in the cracking zone at a temperature of about 590° C. to about 1060° C. to generate cracked products and coke on heat transfer particles, the temperature in the heating zone being greater than the temperature in the cracking zone;
  contacting at least a portion of the cracked products and at least a portion of the heat transfer particles with heat exchange surfaces in a quench zone above the cracking zone to form quenched cracked products, the heat exchange surfaces being at least partially inside the fluidized bed, the heat exchange surfaces comprising an exterior surface of heat exchange tube, a surface of a heat transfer structure different from a heat exchange tube, or a combination thereof; and
  withdrawing a portion of the heat transfer particles from the heating zone and returning the heat transfer particles into at least one of the cracking zone and the quench zone.

2. The method of claim 1, further comprising oligomerizing olefins in the quenched cracked product to form an oligomerized product.

3. A method for performing steam cracking using direct heat transfer, comprising:
  fluidizing a bed of heat transfer particles with a fluidizing gas comprising one or more of steam, oxygen, and a first portion of a hydrocarbon feedstock, the fluidized bed of heat transfer particles comprising a heating zone and a cracking zone above the heating zone;
  exposing the fluidized bed of heat transfer particles to oxygen in the heating zone under oxidizing conditions to generate a temperature in the heating zone of about 760° C. to about 1900° C., at least a portion of the heat transfer particles in the heating zone comprising coke;
  exposing at least a portion of the hydrocarbon feedstock to the fluidized bed of heat transfer particles in the presence of steam in the cracking zone at a temperature of about 590° C. to about 1060° C. to generate cracked products and coke on heat transfer particles, the temperature in the heating zone being greater than the temperature in the cracking zone;
  contacting at least a portion of the cracked products and at least a portion of the heat transfer particles with heat exchange surfaces in a quench zone above the cracking zone to form quenched cracked products, the heat exchange surfaces being at least partially inside the fluidized bed, the heat exchange surfaces comprising an exterior surface of heat exchange tube, a surface of a heat transfer structure different from a heat exchange tube, or a combination thereof;
  oligomerizing olefins in the quenched cracked product to form an oligomerized product; and
  withdrawing a portion of the heat transfer particles from the heating zone and returning the heat transfer particles into at least one of the cracking zone and the quench zone.

4. The method of claim 2, wherein oligomerizing olefins in the quenched cracked product comprises:
  separating a fraction comprising $C_{5-}$ hydrocarbons from the quenched cracked product; and
  exposing at least a portion of the separated fraction to an oligomerization catalyst under oligomerization conditions to form the oligomerized product.

5. The method of claim 2, wherein oligomerizing olefins in the quenched cracked product comprises oligomerizing olefins in the quenched cracked product to form a mixture of ologimerized product and unreacted quenched cracked product, the method further comprising separating at least a portion of the oligomerized product from the unreacted quenched cracked product to form a remainder product, the remainder product optionally being enriched in CO, $H_2$, or a combination thereof.

6. A method for performing steam cracking using direct heat transfer, comprising:
fluidizing a bed of heat transfer particles with a fluidizing gas comprising one or more of steam, oxygen, and a first portion of a hydrocarbon feedstock, the fluidized bed of heat transfer particles comprising a heating zone and a cracking zone above the heating zone;
exposing the fluidized bed of heat transfer particles to oxygen in the heating zone under oxidizing conditions to generate a temperature in the heating zone of about 760° C. to about 1900° C., at least a portion of the heat transfer particles in the heating zone comprising coke;
exposing at least a portion of the hydrocarbon feedstock to the fluidized bed of heat transfer particles in the presence of steam in the cracking zone at a temperature of about 590° C. to about 1060° C. to generate cracked products and coke on heat transfer particles, the temperature in the heating zone being greater than the temperature in the cracking zone;
contacting at least a portion of the cracked products and at least a portion of the heat transfer particles with heat exchange surfaces in a quench zone above the cracking zone to form quenched cracked products, the heat exchange surfaces being at least partially inside the fluidized bed, the heat exchange surfaces comprising an exterior surface of heat exchange tube, a surface of a heat transfer structure different from a heat exchange tube, or a combination thereof;
separating a fraction comprising $C_{4+}$ olefins from the quenched cracked product to form a remainder product that is enriched in $C_{2+}$ olefins, CO, and $H_2$;
exposing the remainder product to a hydroformylation catalyst under hydroformylation conditions; and
withdrawing a portion of the heat transfer particles from the heating zone and returning the heat transfer particles into at least one of the cracking zone and the quench zone.

7. The method of claim 1, wherein the oxygen-containing stream comprises an oxygen stoichiometric ratio of 0.6 to 1.2.

8. The method of claim 1, where the residence time of the hydrocarbon feedstock in the cracking zone is about 0.1 seconds to about 5.0 seconds; or wherein the average temperature of the cracking zone is lower than the average temperature of the heating zone by about 100° C. or more; or wherein the average temperature of the cracking zone is lower than the average temperature of the heating zone by about 300° C. or less; or a combination thereof.

9. The method of claim 1, wherein the heat exchange surfaces comprise heat exchanger tubes, the fluid inside the heat exchange tubes optionally comprising a portion of the hydrocarbon feedstock.

10. The method of claim 1, wherein the at least a portion of the cracked products are contacted with heat exchange surfaces and a quench liquid, the quench liquid being injected above the heat exchange surfaces.

11. The method of claim 1, a) wherein the heat transfer particles comprise refractory solids, silicon-containing particles, sand, coke, or a combination thereof; b) wherein 50 wt. % or more of the heat transfer particles have a characteristic length of 100 μm or less; or c) a combination of a) and b).

12. The method of claim 1, wherein the hydrocarbon feedstock comprises a whole crude prior to fractionation, or wherein the hydrocarbonaceous feed comprises a T90 distillation point of 560° C. or more, or comprises a T70 distillation point of 560° C. or more, or comprises a T50 distillation point of 560° C. or more, or a combination thereof.

13. The method of claim 1, further comprising adding an additional fuel feed to the heating zone, the additional fuel feed optionally comprising a portion of the hydrocarbon feedstock.

14. The method of claim 1, wherein oxygen is introduced as an oxygen-containing stream having a nitrogen content of 50 vol. % or less, or wherein the oxygen-containing stream comprises 90 vol. % or more of oxygen, or a combination thereof.

15. The method of claim 1, further comprising separating a fraction comprising $CO_2$ from at least a portion of the quenched cracked products; or further comprising separating a fraction comprising ethylene, propylene, or a combination thereof from the quenched cracked products; or a combination thereof.

16. The method of claim 1, wherein the quenched cracked products comprise 1.0 vol. % to 50 vol. % of combined $H_2$ and CO.

17. The method of claim 1, wherein the heating zone is separated from the cracking zone by a gas distribution system, or wherein the cracking zone is in direct contact with the heating zone, a bottom of the cracking zone comprising a mid-point of the fluidized bed.

18. The method of claim 1, wherein the quenched cracked product comprises about 20 vol. % or less of $C_{4-}$ olefins.

* * * * *